United States Patent [19]
Menzel et al.

[11] Patent Number: 5,656,495
[45] Date of Patent: Aug. 12, 1997

[54] EXPRESSION VECTOR FOR HUMAN TOPOISOMERASE I

[75] Inventors: Rolf Menzel, Yardley; Scott T. Taylor, Langhorne, both of Pa.

[73] Assignee: Bristol-Myers Squibb Company, Princeton, N.J.

[21] Appl. No.: 376,164

[22] Filed: Jan. 20, 1995

[51] Int. Cl.$^6$ .......................... C12N 15/70; C12N 1/21; C07H 21/04
[52] U.S. Cl. ........................ 435/320.1; 435/172.3; 435/252.33; 536/23.5; 536/23.7; 536/24.1
[58] Field of Search .................. 435/233, 172.1, 435/172.3, 71.2, 320.1, 252.33, 252.3; 536/23.5, 24.1, 23.7

[56] References Cited

FOREIGN PATENT DOCUMENTS

WO-A8909222 of 0000 WIPO .

OTHER PUBLICATIONS

Stark et al. Multicopy expression vectors carrying the lac repressor gene for regulated high-level expression of genes in *Escherichia coli*. Gene vol. 51 255–267 1987.
S.T. Taylor et al., Gene, vol. 167, Nos. 1 and 2, pp. 69–74, 1995.
E. Rubin et al., Journal of Biological Chemistry, vol. 269, No. 4, pp. 2433–2439, 1994.
P. Benedetti et al., Cancer Research, vol. 53, No. 18, pp. 4343–4348, 1993.
P. D'Arpa et al., Proc. Natl. Acad. Sci. USA, vol. 85, pp. 2543–2547, 1988.
A. M. Knab et al., Journal of Biological Chemistry, vol. 268, No. 30, pp. 22322–22330, 1993.
D. Grana et al., Genetics, vol. 120, pp. 319–327, 1988.
Madden et al. Overexpression of human topoisomerase I in baby hamster kidney cells: hypersensitivity of clonal isolates to camptothecin Cancer Research vol. 52 525–532 1992.
Prentki et sl. In vitro insertional mutagenesis with a selectable DNA fragment Gene vol. 29 303–313 1984.
Y–H. Hsiang et al., Journal of Biological Chemistry, vol. 260, No. 27, pp. 14873–14878, 1985.
B. A. Sampson et al., Genetics, vol. 122, pp. 491–501, 1989.
R. Menzel et al., Cell, vol. 34, pp. 105–113, 1983.
G. J. Pruss et al., Cell, vol. 31, pp. 35–42, 1982.
S. DiNardo et al., Cell, vol. 31, pp. 43–51, 1982.
J. W. Little et al., Cell, vol. 29, pp. 11–22, 1982.
M–A. Bjornsti et al., Cancer Research, vol. 49, pp. 6318–6323, 1989.
L. Zumstein et al., J. Mol. Biol., 191, pp. 333–340, 1986.
M. D. Been et al., J. Mol. Biol., 180, pp. 515–531, 1984.
K. Kirkegaard et al., J. Mol. Biol., 15, pp. 625–637, 1985.
H. Hiasa et al., Journal of Biological Chemistry, vol. 269, pp. 2093–2099, 1994.
G. C. Walker, Microbiological Reviews, vol. 48, No. 1, pp. 60–93, 1984.
O. Huisman et al., Nature, vol. 290, pp. 797–799, 1981.
M.–A. Bjornsti et al., Proc. Natl. Acad. Sci. USA, vol. 84, pp. 8971–8975, 1897.
J. C. Wang, Ann. Rev. Biochem., 54, pp. 665–697, 1985.
H. A. DeBoer et al., Proc. Natl. Acad. Sci. USA, vol. 80, pp. 21–25, 1983.
J. C. Wang et al., Nucleid Acids Research, vol. 11, No. 6, pp. 1773–1790, 1983.
C. J. Kenyon et al., J. Mol. Biol., 160, pp. 445–457, 1982.
J. C. Wang, J. Mol. Biol., 55, pp. 523–533, 1971.
E. Kjeldsen et al., Journal of Biological Chemistry, vol. 263, No. 8, pp. 3912–3916, 1988.
J.C. Wang, Biochemica et Biophysica Acta, 909, pp. 1–9, 1987.
K. Drlica et al., Biochemistry, vol. 27, No. 7, pp. 2253–2259, 1988.
E. Durban et al., Biochemical and Biophysical Research Communications, vol. 111, No. 3, pp. 897–905, 1983.
W. A. Baase et al., Biochemistry, 13, pp. 4299–4303, 1974.
R. E. Depew et al., Journal of Biological Chemistry, vol. 253, No. 2, pp. 511–518, 1976.
J. J. Champoux, Proc. Natl. Acad. Sci. USA, vol. 74, No. 9, pp. 3800–3804, 1977.
Y. Pommier et al., Journal of Biological Chemistry, vol. 266, No. 16, pp. 9418–9422, 1990.

*Primary Examiner*—James Ketter
*Assistant Examiner*—John S. Brusca
*Attorney, Agent, or Firm*—Thomas R. Savitsky

[57] ABSTRACT

Expression vectors for human topoisomerase I and a method for detecting poisons of human topoisomerase I. The vector preferably contains a promoter, DNA coding for human topoisomerase I, DNA coding for a selectable marker, an origin of replication, and lac I$^q$ DNA which encodes a repressor for the promoter.

15 Claims, 2 Drawing Sheets

(R)EcoRI (H)HinDIII (P)PstI (S)SalI (B)BamHI (M)SmaI

Activation of sulA-lac

Activation of sulA-lac

EXPRESSION VECTOR FOR HUMAN TOPOISOMERASE I

BACKGROUND OF THE INVENTION

DNA topoisomerases am ubiquitous enzymes which catalyze the breakage and rejoining of the DNA phosphodiester backbone (J. C. Wang, Annu. Rev. Biochem., 54, pages 665–697, 1985; P.-H. Vosberg, Curr. Top. Microbiol. Immunol, 114, pages 19–102, 1985). These reactions, together with an intervening strand passage event, allow this class of enzymes to alter DNA topology. Intermediates in the strand passage reaction may involve either single or double stranded breaks allowing the classification of topoisomerases into type I and type II enzymes respectively. In eukaryotic cells, including human cells, a single type I enzyme has been described (J. C. Wang, Biochem. Biophys. Acta., 909, pages 1–9, 1987). The bacteria E. coli is known to possess two type I enzymes. One, encoded by the topA gene, is responsible for the major DNA relaxing activity of the cell and is essential in an otherwise wild type E. coli (G. J. Pruss et al., Cell, 31, pages 35–42, 1982; S. DiNardo et al., Cell, 32, pages 43–51, 1982). The second E. coli enzyme, topoisomerase III, is a minor activity encoded by the topB gene which appear to be completely dispensable (H. Hiasa et al., J. Biol. Chem., 269, pages 2093–2099, 1994).

Although the E. coli and human topoisomerase I both catalyze the relaxation of negatively supercoiled DNA, they differ in the details of the reactions they catalyze and share no amino acid sequence homology. The human topoisomerase I ("hTOPI") shows a preference for binding double stranded DNA and proceeds by making a single covalent 3'-phosphodiester intermediate to a tyrosine of the enzyme (M.D. Been et al., J. Mol. Biol. 180, pages 515–531, 1984; W. Baase et al., Biochemistry, 13, pages 4299–4303, 1974; J. J. Champoux, Proc. Natl. Acad. Sci. U.S.A., 74, pages 3800–3804, 1977). The E. coli enzyme ("eTOPI") demonstrates a preference for binding at the junction of double and single stranded regions and proceeds using a single 5'-phosphodiester intermediate (J. C. Wang, J. Mol. Biol., 55, pages 532–533, 1971; K. Kirkegaard et al., J. Mol. Biol., 185, pages 625–637, 1985; R. E. Depew et al., J. Biol. Chem., 253, pages 511–518, 1978). The eTOPI enzyme is very efficient at relaxing highly negatively supercoiled DNA and shows progressively decreasing activity as the substrate DNA becomes more relaxed (J. C. Wang, J. Mol. Biol., 55, pages 531–533, 1971; K. Kirkegaard et al., Proc. Natl. Acad. Sci. U.S.A., 184, pages 625–637, 1985). The hTOPI enzyme relaxes both negatively and positively supercoiled DNA to completion (W. Baase et al., Biochemistry, 13, pages 4299–4303, 1974). The hTOPI enzyme is the target of the antitumor drug camptothecin (CMPT) which traps the covalent phosphotyrosine intermediate of the strand passage reaction (Y.-H. Hsiang, et al., J. Biol. Chem., 260, pages 14873–14878, 1985.). E. coli eTOPI enzyme (K. Drlica et al., Biochemistry, 27, pages 2253–2259) is resistant to CMPT.

It previously has been shown that plasmid born copies of both the yeast (M.-A. Bjornsti et al., Proc. Natl. Acad. Sci. U.S.A., 84, pages 8971–8975, 1987) and human topoisomerase I (M.-A. Bjornsti et al., Cancer Research, 49, pages 6318–6323, 1989) coding sequences possess the capacity to complement a conditional defect in the bacterial topA gene. Subsequent to this study the same group of researchers have pursued the development of yeast model systems for the study of the eukaryotic topoisomerase I (J. Nitiss et al., Proc. Natl. Acad. Sci. U.S.A., 85, pages 7501–7505, 1988; M.-A. Bjornsti et al., Cancer Research, 49, pages 6318–6323, 1989). Heretofore, no E. coli system useful as a model for the expression of hTOPI has been reported. This present invention concerns an E. coli system for the controlled functional expression of hTOPI.

SUMMARY OF THE INVENTION

In one aspect the present invention concerns an expression vector comprising:

(a) hTOPI DNA, (b) a promoter, capable of directing expression of hTOPI, and (c) lac $I^q$ DNA which encodes a repressor for the promoter of (b).

In another aspect the present invention concerns a prokaryotic host cell containing an expression vector comprising:

(a) hTOPI DNA, (b) a promoter, capable of directing expression of hTOPI, and (c) lac $I^q$ DNA which encodes a repressor for the promoter of (b).

In another aspect the present invention concerns a method for detecting a poison of human topoisomerase comprising:

(A) culturing a prokaryotic host cell containing the imp mutation and an expression vector containing hTOPI DNA under conditions sufficient to express human topoisomerase, in the presence of a sample which may contain a poison of human topoisomerase, and (B) monitoring DNA damage of the host cell.

By the term "poison" is meant a compound which traps the hTOPI cleavable-complex intermediate. This phenomenon will be explained in more detail hereinafter.

Figure 1:
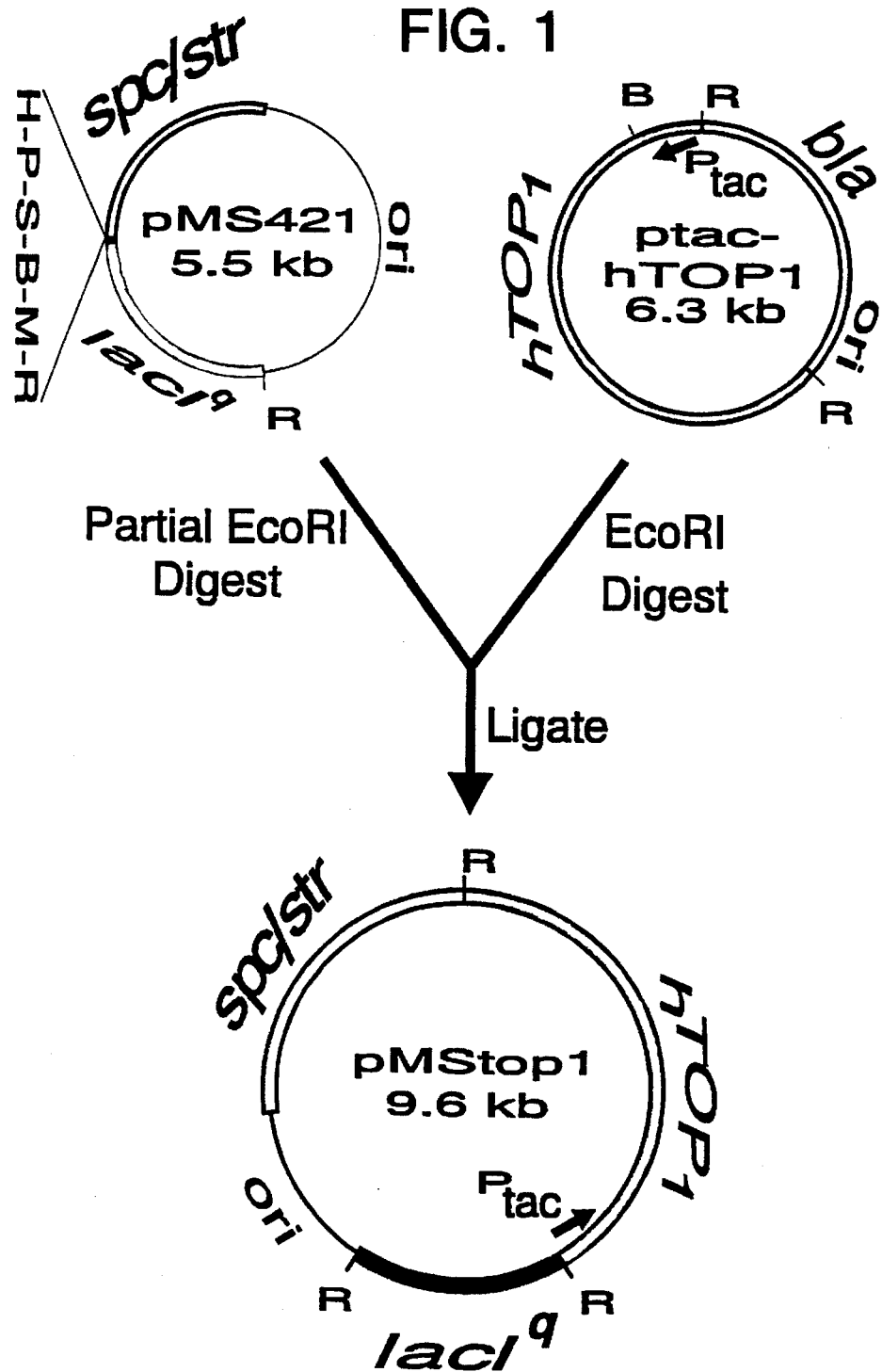
FIG. 1. Construction of a low-copy number regulated hTOPI expressing clone. The plasmid pMS421 was partially digested with EcoRI and the unit sized linear fragments were gel purified. Such linear pMS421 was ligated with EcoRI cut ptac-hTOP, and spectmomycin (SPC) resistant transformants (50 μgram/ml SPC, Sigma) were selected. Several SPC resistant and ampicillin (AP) sensitive transformants were analysed using a battery of mutiple restriction digests. The desired transformant, pMStop1, was identified among these selected transformants. All restriction digests, ligations, gel electrophoresis, plasmid perparations and fragment purification were done according to the vendors recommendations (Promega) and standard procedures (J. Sambrook et al., Molecular Cloning: A Laboratory Manual, Cold Spring Harbor Laboratory, Cold Spring Harbor, N.Y., 1989).

The choice of CPRG allows the rapid determination of β-galactosidase activity in small samples with low levels of activity (D. C. Eustice et al., BioTechniques, 11, pages 739–742, 1991. Assays performed with ONPG give strictly analogous results. The conclusion made from the data shown in this figure can also be reached by using solid agar plates with X-gal in the agar to indicate β-galactosidase activity. Strain construction.

The E. coli strain GR4413 (sulA-lac; O. Huisman et al., Nature, 290, pages 797–799, 1981) had the imp4312 mutation introduced by transduction as described in the legend to Table 2 (see Example 3) and was then transformed with the plasmid pMStop1 (LB-SPC at 25 μgram/ml) to produce strain 2055A. E. coli strain 2055A was deposited with the American Type Culture Collection (ATCC), 12301 Parklawn Drive, Rockville, Md., U.S.A., on Dec. 13, 1994, under the provisions of the Budapest Treaty, and has the accession number ATCC 69736.

DETAILED DESCRIPTION OF THE INVENTION

The present invention concerns an expression vector containing hTOP1 DNA, i.e., DNA coding for part or all of human topoisomerase I (hTOP1). Preferably, the hTOP1 DNA is cDNA.

The expression vectors of the invention comprise regulatory DNA sequences, such as the promoter and repressor, operatively linked to the DNA sequence coding for all or part of hTOPI. Other regulatory sequences optionally present are also operatively linked to the DNA sequence coding for all or part of hTOP1. As used in this context, the term "operatively linked" means that the regulatory DNA sequences are capable of directing the replication and/or the expression of the DNA sequence coding for all or part of hTOPI.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front of (i.e., upstream of) the DNA sequence and followed by the DNA sequence coding for all or part of hTOPI transcription, termination sequences and the remaining vector. The expression vector of the invention also preferably contains a marking sequence(s) which is capable of providing phenotypic selection in transformed host cells (i.e., a selectable marker). The expression vector of the invention also contains a sequence which allows expression of hTOPI gene to be modulated (i.e., the lac $I^q$ repressor). The expression vectors may also include other DNA sequences known in the art, for example, stability leader sequences which provide for stability of the expression product, secretory leader sequences which provide for secretion of the expression product, stability elements which provide mitotic stability to the plasmid, and sequences which provide sites for cleavage by restriction endonucleases. The characteristics of the actual expression vector used must be compatible with the host cell which is to be employed.

The DNA coding for hTOP1 is well known in the art, for example, the sequence is disclosed in D'Arpa, P. et al. Proc. Natl. Sci. U.S.A. 85 p. 2543–2547, 1987 and Bjornsti, M.-A. et al., Cancer Reserach 49, p. 6318–6323, 1989.. The promoters useful herein are well known in the art and are chosen to be operable in the host cell of choice. Preferred promoters include, for example, lac, trp and most preferred tac. The sequences for the promoters are described in, for example, Weiss et al. Proc. Natl. Acad. Sci. U.S.A. 81, p. 6019–6023, 1984.

The expression vector of the invention also preferably contains a DNA sequence coding for a selectable marker. The particular selectable marker used is not critical provided the marker allows for phenotypic selection in transformed host cells. For convenience, preferred selectable markers are antibiotic resistance. Examples of antibiotic resistance selectable markers include ampicillin, tetracycline, kanamycin, chloramphenicol, spectinomycin. Most preferred is streptomycin resistance, spectinomycin resistance or both.

The expression vector of the invention also contains lac $I^q$ DNA which encodes a repressor. The repressor DNA sequence is disclosed in Farabaugh, Nature 274, p. 765–769, 1978.

Particularly preferred is the expression vector designated pMStopI, described in FIG. 1, which contains the DNA sequence coding for hTOPI, or expression vectors with the identifying characteristics of pMStopI.

Suitable expression vectors containing the desired coding and control sequences may be constructed using standard recombinant DNA techniques as taught herein or as known in the art, many of which are described in T. Maniatis et al., Molecular Cloning: A Laboratory Manual, Cold Spring Harbor Laboratory, Cold Spring Harbor, N.Y., 1982.

The present invention additionally concerns host cells containing an expression vector which comprises a DNA sequence coding for all or part of hTOPI. The host cells preferably contain the pMStopI expression vector as shown in FIG. 1. Further preferred are host cells containing an expression vector comprising one or more regulatory DNA sequences capable of directing the replication and/or the expression of and operatively linked to a DNA sequence coding for all or part of hTOPI. Suitable host cells are prokaryotic cells which are preferably biologically pure. Suitable prokaryotic host cells include, for example, *Escherichia coli, Bacillus subtilus* and *Salmonella typhimurum* cells. The most preferred host cell of the invention is *E. coli* ATCC 69736. *E. coli* ATCC 69736 (also known as strain 2055A, RFM2055, or SBG 1398) was deposited with the American Type Culture Collection, 12301 Parklawn Drive, Rockville, Md., U.S.A. 20852 on Dec. 13, 1994, under the provisions of the Budapest Treaty. *E. coli* ATCC 69736 contains plasmid pMStop1, a chromosomal sulA-lac insertion, and the chromsomal imp 4312 mutation.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection, viral or phage infection or protoplast fusion, can also be employed.

Once an expression vector has been introduced into an appropriate host cell, the host cell may be cultured under conditions permitting expression of the desired polypeptide, in this case a polypeptide molecule comprising all or part of hTOPI.

Host cells containing an expression vector which contains a DNA sequence coding for all or part of hTOPI may be identified by one or more of the following six general approaches: (a) DNA-DNA hybridization; (b) the presence or absence of marker gene functions; (c) assessing the level of transcription as measured by the production of hTOPI mRNA transcripts in the host cells; (d) detection of the gene product immunologically; (e) complementation analysis; and (f) enzyme assay, enzyme assay being the preferred method of identification.

In the first approach, the presence of a DNA sequence coding for all or part of hTOPI can be detected by DNA-DNA or RNA-DNA hybridization using probes complementary to the DNA sequence.

In the second approach, the recombinant expression vector host system can be identified and selected based upon the presence of absence of certain maker gene functions (e.g., thymidine kinase activity, resistance to antibiotics, uracil prototrophy, etc.). A marker gene can be placed in the same plasmid as the DNA sequence coding for all or part of hTOPI under the regulation of the same or a different promoter used to regulate the hTOPI coding sequence. Expression of the marker gene in response to induction or selection indicates expression of the DNA sequence coding for all or part of hTOPI.

In this third approach, the production of hTOPI mRNA transcripts can be assessed by hybridization assays. For example, RNA can be isolated and analyzed by Northern blotting or nuclease protection assay using a probe complementary to the RNA sequence. Alternatively, the total nucleic acids of the host cell may be extracted and assayed or hybridization to such probes.

In the fourth approach, the expression of all or part of hTOPI can assessed immunologically, for example, by Western blotting.

In the fifth approach, the expression of hTOPI protein can be assessed by complementation analysis. For example, in cells known to be deficient in this enzyme, expression of hTOPI activity can be inferred by improved growth of cells under growth-limiting conditions.

In the sixth approach, expression of hTOPI can be measured by assaying for hTOPI enzyme activity using known methods. For example, the assay described in Y. Pommier, J. Biol. Chem., 265, pages 9418–9422, 1990 may be employed.

The DNA sequences of expression vectors, plasmids or DNA molecules of the present invention may be determined by various methods known in the art. For example, the dideoxy chain termination method as described in Sanger et al., Proc. Natl. Acad. Sci. U.S.A., 74, pages 5463–5467, 1977, or the Maxam-Gilbert method as described in Proc. Natl. Acad. Sci. U.S.A., 74, pages 560–564, 1977 may be employed.

It should, for course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for detecting posion of hTOPI. The term "poison" means a compound which traps the cleavable-complex intermediate. The "cleavable-complex intermediate" is formed when an hTOPI poison traps the covalent phosphotyrosine DNA-protein intermediate of the strand passage reaction. A typical example of a poison is CMPT.

Previously, it has been known that eTOPI enzyme is resistant to CMPT. We have also found that the bacterium, $E.\ coli$, is also resistant to CMPT. Prior art plasmids containing DNA coding for hTOPI are detrimental to bacteria, and $E.\ coli$ in particular, and prior art plasmids are not stable. Such prior art plasmids are detrimental to bacteria because of topological problems resulting from an imbalance in DNA relaxing and DNA supercoiling activities. By use of the expression vector of the present invention, a lower copy number is achieved. Furthermore, the use of lac $I^q$ gene with its repressor results in a more controllable expression system. The expression system of the invention is more controllable because the copy number of the hTOPI gene has been reduced by using a reduced copy number plasmid and the lac $I^q$ gene has been provided on the same plasmid to insure elevated levels.

In the process of the invention, the host cell has an imp mutation, for example, the imp 4213 mutation. The imp mutation is described in B. A. Sampson et al., Genetics, 122, pages 491–501, 1989. We have found that using host cells with the imp mutation allows for entry of CMPT and similar compounds into the cells. As a result, bacteria such as $E.\ coli$ can demonstrate sensitivity to CMPT and like drugs.

Moreover, in the process of the invention we note that DNA damage resulting from the addition of CMPT, if and only if hTOP is induced, can be detected through the induction of DNA damage. Inducible promoters such as sulA which is a part of the so-called SOS response can be used to detect such damage. We also infer that DNA damage has occurred in response to CMPT under the above defined conditions by the elevated cytotoxicity noted in a strain defective in DNA repair due to a loss of the recA gene.

in the process of the invention for detecting a poison to hTOPI, DNA damage is monitored. This can be accomplished by quantitating increases in the expression of the sulA gene. This can conveniently be performed by monitoring β-galactosidase production, for example, by monitoring a chromophor color change. Thus, in the method of the invention it is preferred that the host cell has a SOS responsive sulA-lac fusion.

The following examples are to illustrate the invention but should not be interpreted as a limitation thereon.

EXAMPLE 1

$E.\ coli$ expresses phenotypes based on the expression of hTOPI.

M.-A. Bjornsti et al., Cancer Research, 49, pages 6318–6323 (1989) have shown that the expression of an hTOP1 clone in $E.\ coli$ can reverse the growth defect seen at 42° C. in a topA amber mutant that was suppressed by a temperature sensitive amber suppressor. In a similar fashion we show the suppression of another phenotype associated with a defect resulting from the deletion of the topA gene.

It has been shown that a deletion of the topA gene cannot be inherited in a wild type *E. coli* but that certain defects in the gyrA or gyrB genes, which result in reduced DNA supercoiling, are able to allow the inheritance of a topA deletion (G. J. Pruss et al., Cell, 31, pages 35–42, 1982; S. DiNardo et al., Cell, 31, pages 43–51, 1982). The loss of the topA gene results in the loss of the cell's major DNA relaxing activity and, apparently, this loss is not viable unless balanced by a reduction in cell's capacity to supercoil DNA. The topA-deletion phenotype used herein is based on a strain in which a conditional defect in the gyrB gene is able to act as a conditional compensatory mutation for a topA deletion. The strain RFM475, which has both a temperature sensitive defect in the gyrB gene (gyrB221 gyrB203) and a deletion in the chromosome that removes the topA and cysB genes (Δcystop), is both temperature sensitive and cold sensitive. The temperature sensitive character of RFM475 is not unexpected as the gyrB gene product is temperature sensitive (R. Menzel et al., Cell, 34, pages 105–113, 1983). The cold sensitive phenotype is novel. At 37° C. the mutant gyrase allele is defective but retains enough activity to allow the strain to grow, and this reduced activity allows the inheritance and stable maintenance of the topA deletion. Lowering the temperature of the strain to 25° C. results in the mutant gyrase regaining a more wild type level of activity and the strain is unable to grow at 25° C.

The ability to observe transformants at 250° C. in RFM475 (ΔtopA gyrB221 gyrB203) is used herein as a phenotypic means of demonstrating that a plasmid carries DNA relaxing activity. Table I shows that the plasmid pUC19 is able to transform the strain RFM475 to ampicillin (AP) resistance only at 37° C., whereas, in the strain RFM445 (gyrB221 gyrB203 topA$^+$) AP resistant transformants are obtained at both 25° C. and 37° C. Using a control plasmid (pID35; K. Becherer et al., Nucl. Acids Res., 11, pages 1773–1790, 1983; L. Zumstein et al;, J. Mol. Biol., 191, pages 333–340, 1986) which contains a truncated, but active, form of the *E. coli* topA gene transformants are obtained in both RFM475 and RFM445 at 25° C. and 37° C. The truncated version of the *E. coli* topA gene is able to suppress the cold sensitive defect of RFM475. (The truncated version of topA is used because full length topA clones on a high copy number plasmid show stability problems). The hTOPI cDNA clone (obtained from Jim Wang; M. A. Bjornsti et al., Proc. Natl. Acad. Sci. U.S.A., 84, pages 8971–8975, 1987) is able to give AP-resistant transformants at 25° C. in the gyrB$^{TS}$ ΔtopA strain. In addition it is noted that it is not able to observe transformants with the gyrB$^{TS}$ topA$^+$ strain using the hTOPI cDNA clone when the transformation mixture is plated at 37° C. while normal transformation is noted at 25° C. in this genetic background. Apparently the addition of more DNA relaxing activity to a strain with a defect in DNA supercoiling, in the case of the hTOPI clone, can extend the lethal range of the gyrB$^{TS}$ gyrase allele to 37° C. It is worth noting that while the eTOPI clone (pID35) is able to suppress the cold sensitivity of RFM475, it does not extend the temperature sensitivity of the gyrB$^{TS}$ allele to 37° C. Table 1 shows two phenotypes consistent with the hTOPI cDNA clone demonstrating DNA relaxing activity in *E. coli*: the ability to suppress the cold sensitivity associated with the loss of topA and the potential to extend the lethal range of a gyrB$^{TS}$ allele.

The reason for using the ability to obtain transformants in a particular genetic background to demonstrate that a gene carried on a plasmid has certain phenotypes, in this instance, associated with DNA topology ties in the unstable character of the transformants that are obtained with the ptac-hTOP plasmid.

TABLE 1

| Host Strain | Plasmid | Transformants @ 25° C. | @ 37° C. | @ 42° C. |
| --- | --- | --- | --- | --- |
| RFM443 | pUC19 | YES | YES | YES |
| gyrB$^+$ topA+ | pID35 (eTOPI) | YES | YES | YES |
|  | ptac-hTOPI | YES* | YES* | YES* |
| RFM445 | pUC19 | YES | YES | NO |
| gyrB$^{TS}$ topA$^+$ | pID35 (eTOPI) | YES | YES | NO |
|  | ptac-hTOPI | YES* | NO | NO |
| RFM475 | pUC19 | NO | YES | NO |
| gyrB$^{TS}$ Δtop | pID35 (eTOPI) | YES | YES | NO |
|  | ptac-hTOPI | YES* | YES* | NO |

The plasmid ptac-hTOP can demonstrate phenotypes consistent with the introduction of DNA relaxing activity. The indicated strains were transformed with either pUC19 (no insert), pID35 (a clone with a truncated, but active, version the *E. coli* topA gene extending from the PstI site upstream of the topA gene to the EcoRI site within the carboxyl domain of the topA gene cloned into pBR322, K. Becherer et al., Nucl. Acids Res. 11, pages 1773–1790, 1983; L. Zumstein et al., J. Mol. Biol., 191, pages 333–340, 1986), or ptac-hTOP (a full length cDNA clone of the gene for hTOPI expressed from a tac promoter, M.-A. Bjorntsi et al., Cancer Research, 49, pages 6318–6323, 1989) on LB-agar plates (T. J. Silhavy et al., Experiments with Gene Fusions, Cold Spring Harbor Laboratory, Cold Spring Harbor, N.Y., 1984) with 50 μgram/ml AP. All strains were made competent using standard CaCl$_2$ methods (J. Sambrook et al., Molecular Cloning: A Laboratory Manual, Cold Spring Harbor Laboratory, Cold Spring Harbor, N.Y., 1989) and 2×10$^8$ cells were transformed with 10 nanograms of CsCl$_2$ banded plamsid DNA (J. Sambrook et al., Molecular Cloning: A Laboratory Manual, Cold Spring Harbor Laboratory, Cold Spring Harbor, N.Y., 1989). After a 5 minute heat shock at 37° C., a 0.1× aliquot of the mixture was plated at the indicated temperatures. Plates were score for the inheritance of the plasmid (AP$^R$) at the indicated temperatures after 16 hours for the 37° C. and 42°0 C. plates, and after 24 hours for the 25° C. plates. A "YES" in the table indicates that 100–1000 uniform smooth rounded colonies with modest colony size variation appeared. A "YES*" indicates that 100–1000 transformants with irregular colony morphology and vastly different sizes showing frequent fast growing papillae arose. A "NO" indicates that transformants were not observed following the designated incubation times. Host strains.

The gyrB+ topA+ recipient is RFM443 which is a Δlac74 version of the *E. coli* wild type N99 or W3102 (Bachman, B. J., Derivation and genotypes of some mutant derivatives of *Escherichia coil* K-12. pages 1190–1220 in, *Escherichia coil* and *Salmonella typhimurium* cellular and molecular biology. Chief Editor, F. C. Neidhardt, ASM Press 1987). The gyrB$^{TS}$ topA+ recipient is RFM445, a Δlac74 version of N4157 (an N99/W3102 derivative) containing the defective gyrase allele (gyrB221, gyrB203) previously described (R. Menzel et al., Cell, 34, pages 105–113, 1983).

The strain RFM475 was constructed as follows: N4157 was transduced with phage P1 vir grown on PLK831 to pyrF ΔtrpE zci-Tn 10 by for selecting tetracycline resistance. An appropriate transductant from that cross was tranduced to Pyr+ with phage grown on N99 and a ΔtrpE-tetracycline sensitive transductant was retained as RFM431. RFM431 was transduced to Trp+ with phage grown on DM800

(ΔcysBtopA, S. DiNardo et al., Cell, 31, pages 43–51, 1982) and a Cys-(ΔcysBtopA) transductant was made Δlac74 as described below and kept as RFM475. (RFM431, 443, 445, and 475 are also described in M. Drolet et al., Proc. Natl. Acad. Sd. U.S.A., 1995 in press).

Reduced hTOPI expression leads to more stable strains.

Expression of the hTOPI gene in the plasmid ptac-hTOP is directed by the strong synthetic tac promoter. This promoter is subject to regulation by the lac I gene (H. A. deBoer et al., Proc. Natl. Acad. Sci. U.S.A., 80, pages 21–25, 1983, but when present on a high copy number plasmid a single chromosomal copy of the lac I gene is not sufficient to repress expression. Extra copies of the lac I gene on second plasmids (F'lac $I^q$ and pMS421) were provided and copy of the over-expressing lac $I^q$ gene was cloned onto the plasmid ptac-hTOP. Neither of these approaches would yield stable transformants. Apparently the basal repressed expression of the hTOPI gene from the ptac-hTOPI construct is not well tolerated in a wild type E. coli. To reduce this basal expression the hTOPI gene from ptac-hTOP was into the subcloned lower copy number plasmid pMS421 (pMS421 has a pSC101-origin of replication and the lac $I^q$ gene; D. Graña et al., Genetics, 120, pages 319–327, 1988) as illustrated in FIG. 1. In the absence of the tac inducer, IPTG, transformants of our subclone, pMStopI, are uniform in colony size and morphology, and appear to be completely stable. Upon the addition of IPTG (0.1–1 mM) the complementation patterns and plasmid instability discussed above reappear. Recloning the gene from a pUC-based to a pSC101-based plasmid, together with the introduction of a tighter repression control, allows for the stable repressed inheritance of the hTOPI gene in E. coli, while permitting the IPTG induced expression of phenotypes when required.

EXAMPLE 3

A strain with PMStopI can be made to show an inducible camptothecin sensitivity.

The eukaryotic type I topoisomerases are unique in their ability to relax DNA in the absence of a divalent cation and the inclusion of a chelating agent, such as EDTA, assures that only eukaryotic topoisomerase I is being assayed (P.-H. Vosberg, Curr. Top. Microbiol. Immunol., 114, pages 19–102, 1985; M.-A. Bjornsti et al., Proc. Natl. Acad. Sci. U.S.A., 84, pages 8971–8975, 1987). Crude lysates prepared from cells harboring pMStopI grown in the presence of 1 mM IPTG demonstrate abundant EDTA-resistant DNA relaxing activity, while the same cells grown without IPTG fail to demonstrate (<5% induced levels) such activity (data not shown). Furthermore, the EDTA resistant DNA relaxing activity expressed upon IPTG induction is inhibited by the anti-cancer drug CMPT. CMPT inhibits hTOPI by trapping an enzyme-DNA intermediate in the so-called cleavable complex (Y.-H. Hsiang et al., J. Biol. Chem., 260, pages 14873–14878, 1985; and E. Kjeldsen et al., Characterization of a camptothecin-resistant human DNA topoisomerase I., J. Biol. Chem., 263, pages 3912–3916, 1988). In vitro the enzyme-DNA, intermediate trapped in such a cleavable complex can be provoked to demonstrate single stranded breaks by the addition of a protein denaturant such as SDS (Y.-H. Hsiang et al., J. Biol. Chem., 260, pages 14873–14878, 1985). In vivo, activities in eukaryotic cells, such as DNA replication, process the cleavable complex into extensive DNA damage which results in cell death (L. Liu, Annu. Rev. Biochem., 58, pages 351–375, 1989). Since bacteria harboring pMStopI grown in the presence of IPTG contain a CMPT sensitive DNA relaxing activity, it was reasoned that such cells should be sensitive to the effects of the CMPT. Initial experiments failed to demonstrate any CMPT sensitivity for cells harboring pMStopI grown in the presence of 1 mM IPTG (see Table 2).

There could be many reasons for the hTOPI-expressing bacteria failing to demonstrate CMPT sensitivity. One such reason could be lack of permeability to CMPT. Several genetic backgrounds and mutations were tried in an effort to demonstrate an inducible CMPT sensitivity with the pMStopI plasmid. The highest level of sensitivity was found when the imp4213 mutation was introduced. The imp mutant was originally isolated by selecting for increased permeability to maltodextran and was subsequently shown to have dramatically increased sensitivity to several drugs and chemical agents (B. A. Sampson et al., Genetics, 122, pages 491–501, 1989). The imp mutation was mapped to minute 2 on the E. coli map but the biochemical nature of the lesion is not known (B. A. Sampson et al., Genetics, 122, pages 491–501, 1989; Benson, personal communication). In Table 2 the combination of the imp4213 mutation, the plasmid pMStopI, and growth with IPTG are shown to be all necessary for a CMPT sensitive E. coli.

TABLE 2

| Strain | imp+/pMStop1 | | imp 4213/ pMS421 | | imp 4213/ pMStop1 | |
|---|---|---|---|---|---|---|
| IPTG | None | +1 mM | None | +1 mM | None | +1 mM |
| Camptothecin | | | | | | |
| 200 µg/ml | 4 | 4 | 7 | 7 | 7 | 15 |
| 50 | 4 | 4 | 7 | 7 | 7 | 13 |
| 25 | 4 | 4 | 7 | 7 | 7 | 11 |
| 12 | 4 | 4 | 7 | 7 | 7 | 9 |
| 6.2 | 4 | 4 | 7 | 7 | 7 | 7 |
| None | 4 | 4 | 7 | 7 | 7 | 7 | hTOPI expression and an imp defect are required for CMPT sensitivity. 10 cm petri dishes with 40 ml of LB-agar plus 50 µgram/ml AMP, with (1 mM) or without IPTG, were overlayed with $10^8$ midlog cells of the designated genotype in 4ml of soft (0.7% agar) LB-agar at 48° C. When the soft-agar overlays had solidified, 4 mm cylindrical holes were cored to the bottom surface of the petri dish using a small probe attached to a vacuum. 20 ul samples of CMPT (Sigma) dissolved in DMSO at the concentrations indicated were applied to these wells; "None" indicates a DMSO-alone control. After 16 hours at 30° C., the zones of clearing (no cell growth) around the wells were measured and are recorded as millimeters of diameter in the table. The 4 mm value for the imp+/pMStop1 strain is simply the diameter of the well. The 7 mm value noted for both imp4213 strains in the "None" row, DMSO-alone control, shows that the imp defect confers a low level of sensitivity to 100% DMSO.

Strains used.

The imp+/pMStop1 strain is N99 transformed with pMStop1. An imp4213 derivative of E. coli strain N99 was constructed by growing P1 vir on BAS1329 (imp4213 leu::Tn 10, B. A. Sampson et al., Genetics, 122, pages 491–501, 1989) and transducing N99 to tetracycline resistance and screening for coinheritence of the imp phenotype as described in Sampson et al. 1989. Such an imp-strain was then transduced to protrophy (Leu+) and an imp4213 version was retained as RFM795. The strains imp4213/pMS421 and imp4213/pMStop1 are RFM795 transformed with pMS421 and pMStop1 respectively (on LB-agar selecting SPC, resistance at 25 µgram/ml).

EXAMPLE 4

Camptothecin sensitivity In *E. coli* Involves DNA damage.

The pathway leading from the formation of the CMPT-induced cleavable complex to cell death involves DNA damage (L. Liu, Annu. Rev. Biochem., 58, pages 351–375, 1989). This has been demonstrated in the yeast *S. cerevisiae* through the elevated CMPT sensitivity seen in a DNA damage repair deficient rad52 mutant and through the induction of a DNA damage inducible promoter following exposure to CMPT (J. Nitiss et al., Proc. Natl. Acad. Sci. U.S.A., 85, pages 7501–7505, 1988; W.-W. Eng et al., Mol. Pharm., 34, pages 755–760, 1989). We are able to make similar observations in *E. coli* strains harboring the pMStopI plasmid.

In *E. coli* the activation of the recA gene product and the subsequent inactivation of the lexA repressor am primary events in the induction of many enzymes involved in the repair of DNA damage (J. W. Little et al., Cell, 29, pages 11–22, 1982). Mutants defective in recA consequently exhibit enhance sensitivity to many DNA damaging agents (G. A. Walker, Microbiol. Rev. 48, pages 60–93, 1984). In Table 3 it is demonstrated that an *E. coli* strain with a defect in the recA gene shows 50-fold enhanced sensitivity to CMPT when the expression of hTOPI is induced. Presumably with a recA defect the repair of CMPT-induced damage does not occur and such a strain is, therefore, more sensitive (than a $recA^+$ strain) to the effects of this antitumor drug when hTOPI is present.

Figure 2A:
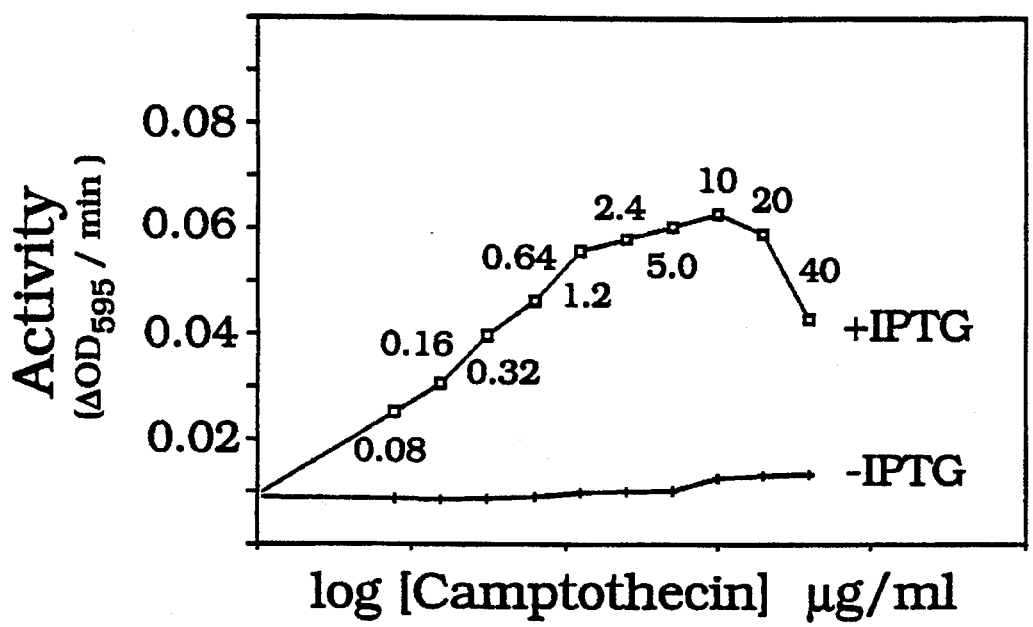
FIGS. 2A and 2B. Camptothecin ("CMPT") can induce sulA-lac when hTOPI is expressed. The strain RFM2055 (imp4312 sulA-lac/pMStop1) was grown overnight in LB liquid media (T. J. Silhavy et al., Experiments with Gene Fusions, Cold Spring Harbor Laboratory, Cold Spring Harbor, N.Y., 1984) with 25 μgram/ml SPC, diluted 1:100 the next morning into LB without SPC and then grown into midlog phase as an inoculum in the experiment. This culture ($OD_{650}$=0.6) was diluted 1:100 into fresh LB liquid with (1 mM) and without (IPTG). 190 μl aliquots (±IPTG) were added to duplicate 10 μl samples of drug (in 100% dimethylsulfoxide ("DMSO") distributed in the wells of a microtiter plate. The microtiter plate is incubated overnight at 300° C. without shaking. Following this growth and drug exposure, final cell $OD_{650}$ values are determined, the cells are permeablized with $CHCl_3$, and assayed for β-galactosidase activity essentially as described by R. Menzel, Anal. Biochem., 181, pages 40–50, 1989 with the following exception: the substrate chlorophenol red (CPRG) was substituted for o-nitropheno-β-galactoside ("ONPG") and the assay's progress was monitoered by following the change in $OD_{595}$. Final activities were calculated from a kinetic assay (with nine time points) and expressed as $\Delta OD_{595}$/min. The upper graph (FIG. 2A) shows the induction of β-galactosidase activity by the drug CMPT at the concentrations given in the figure. The lower graph (FIG. 2B) shows the induction of β-galactosidase activity by the DNA gyrase inhibitor, nalidixic acid, at the concentrations given in the figure.
Figure 2B:
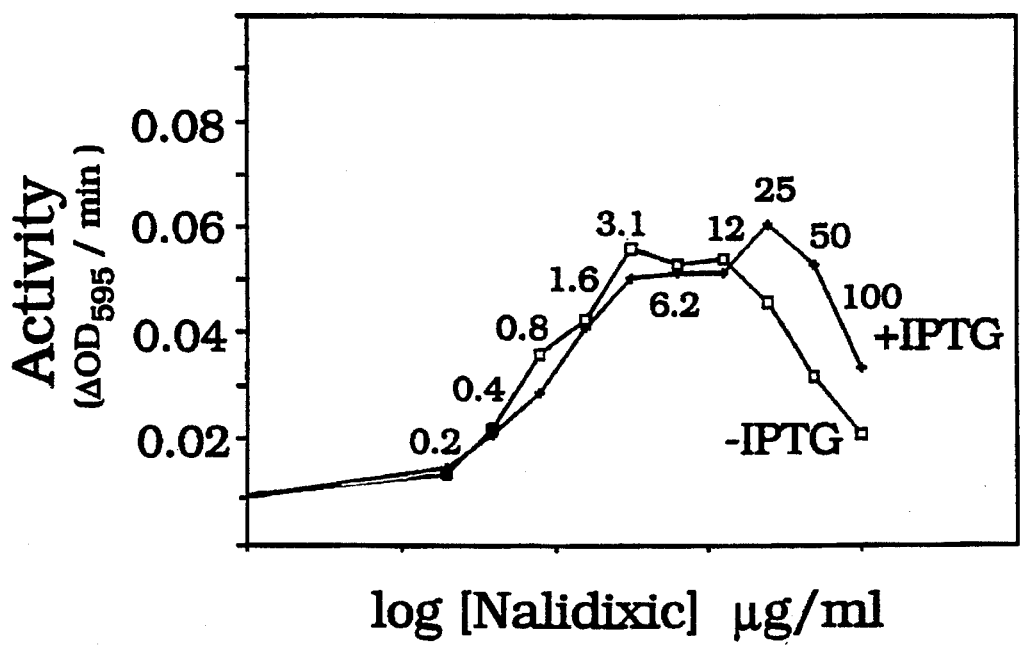

The sulA gene product is able to inhibit cell division and its induction following DNA damage is thought to allow the cell sufficient time for DNA repair to occur prior to the next cell division (Huisman and D'Ari, 1982). Measuring increases in β-galactosidase activity directed by a sulA-lac gene fusion is an established method for monitoring DNA damage (Kenyon et al., 1982). In FIG. 2A we show that CMPT is able to induce sulA only when hTOPI is present. This behavior stands in contrast to other DNA damaging agents, such as nalidixic acid (FIG. 2B), which do not depend on the expression of hTOPI. The hTOPI dependence of a number of known DNA damaging agents was examined and only CMPT has a signal which is dependent upon the induction of hTOPI (data not shown). Most DNA damaging agents show a reduced capacity (0.5× to 0.9×) to induce sulA-lac when hTOPI is expressed (data not shown), and the basal (uninduced) level of sulA expression declines 20% upon hTOPI induction. This is a result of the fact that hTOPI expression is detrimental to *E. coli* and less robust *E. coli* are less able to express or increase expression of sulA.

TABLE 3

| Strain | rec $A^+$ | | rec $A^-$ | |
|---|---|---|---|---|
| IPTG | None | 1 mM | None | 1 mM |
| Camptothecin | | | | |
| 25 µg/ml | 7 | 11 | 7 | >20 |
| 10 | 7 | 7 | 7 | 17 |
| 5 | 7 | 7 | 7 | 16 |
| 2.5 | 7 | 7 | 7 | 14 |
| 1.2 | 7 | 7 | 7 | 13 |
| 0.63 | 7 | 7 | 7 | 11 |
| 0.31 | 7 | 7 | 7 | 9 |
| None | 7 | 7 | 7 | 7 |

A recA defect elevates CMPT sensitivity. The strain RFM795 (as described for Table 2) was transduced to tetracycline resistance with P1 vir grown on a strain with the ΔsrlrecA srl::dTn 10 mutation (a deletion of recA generated from a Tn 10 in srl) to obtain a recA defective version of RFM795. Both Rec- and Rec+ versions were transformed with pMStop1 (selected on 25 µgram/ml SPC LB-agar) to obtain the strains used. Plates, agar overlays, and sample application was performed as described for Table 2. The results show that 0.63 µgrams/ml CMPT gives the same IPTG-dependent zone of inhibition in the recA defective strain as noted at 25 µgrams/ml in the recA+ strain.

What is claimed is:

1. An expression vector comprising:
   (a) DNA encoding human topoisomerase I (hTOPI),
   (b) a promoter which directs expression of hTOPI, and
   (c) lac $I^q$ DNA which encodes a repressor for the promoter of (b).

2. The expression vector of claim 1 wherein the hTOPI DNA is cDNA.

3. The expression vector of claim 1 further comprising an origin of replication and a DNA sequence which encodes a selectable marker.

4. The expression vector of claim 3 wherein the selectable marker is antibiotic resistance.

5. The expression vector of claim 3 wherein the selectable marker is streptomycin resistance, spectinomycin, resistance or both.

6. The expression vector of claim 1 wherein the promoter is lac, trp or tac.

7. The expression vector of claim 1 which is plasmid pMStopI.

8. A prokaryotic host cell containing an expression-vector comprising:
   (a) DNA encoding human topoisomerase I (hTOPI),
   (b) a promoter which directs expression of hTOPI, and
   (c) lac $I^q$ DNA which encodes a repressor for the promoter of (b).

9. The prokaryotic host cell of claim 8 which is *E. coli*.

10. The *E. coli* host cell of claim 9 which contains an imp mutation.

11. The *E. coli* host cell of claim 10 wherein the imp mutation is imp 4213 mutation.

12. The *E. coli* host cell of claim 8 wherein the expression vector further comprises an origin of replication and a DNA sequence which encodes a selectable marker.

13. The *E. coli* host cell of claim 12 wherein the hTOPI DNA is cDNA, the selectable marker is antibiotic resistance to streptomycin, spectinomycin, or both, and the promoter is lac, trp, or tac.

14. The *E. coli* host cell of claim 8 wherein the expression vector is plasmid pMStopI.

15. *E. coli* ATCC 69736.

* * * * *